United States Patent
Hartmann et al.

(10) Patent No.: US 7,045,330 B2
(45) Date of Patent: May 16, 2006

(54) DNA SEQUENCE OF THE ENZYME PHOSPHOLIPASE A1 OF CILIATE TETRAHYMENA, AND THE USE OF THE SAME

(75) Inventors: Marcus Hartmann, Münster (DE); Marco Grenningloh, Mainz (DE); Arno Tiedtke, Münster (DE)

(73) Assignee: Cilian AG, Munster (DE)

( * ) Notice: Subject to any disclaimer, the term of this patent is extended or adjusted under 35 U.S.C. 154(b) by 0 days.

(21) Appl. No.: 10/466,110

(22) PCT Filed: Jan. 22, 2002

(86) PCT No.: PCT/EP02/00578

§ 371 (c)(1),
(2), (4) Date: Dec. 31, 2003

(87) PCT Pub. No.: WO02/057459

PCT Pub. Date: Jul. 25, 2002

(65) Prior Publication Data

US 2004/0115673 A1  Jun. 17, 2004

(30) Foreign Application Priority Data

Jan. 22, 2001  (DE) .............................. 101 05 152

(51) Int. Cl.
*C12N 9/20* (2006.01)
*C12N 1/20* (2006.01)
*C12N 15/00* (2006.01)
*C07H 21/04* (2006.01)

(52) U.S. Cl. ................ 435/198; 435/252.3; 435/320.1; 536/23.2

(58) Field of Classification Search ................ 435/198, 435/252.3, 320.1; 536/23.2
See application file for complete search history.

(56) References Cited

FOREIGN PATENT DOCUMENTS

JP          10 155493          6/1998

OTHER PUBLICATIONS

Guberman et al., "A method for the preparation of *Tetrahymena thermophila* phospholipase $A_1$ suitable for large-scale production", Journal of Applied Microbiology, 86 (1999), 226-230.

Hartmann et al., "Screening for and characterization of phospholipase $A_1$ hypersecretory mutants of *Tetrahymena thermophila*", 54 (2000), 390-396.

J. Florin-Christensen, et al., "Phospholipase $A_1$ and Triacylglycerol Lipase: Two Novel Enzymes From Tetrahymena Extracellular Medium," Comp. Biochem. Physiol., vol. 85B, No. 1, pp. 149-155, 1986, [XP001053004].

*Primary Examiner*—Tekchand Saidha
(74) *Attorney, Agent, or Firm*—Jacobson Holman PLLC

(57) ABSTRACT

A nucleic acid coding for the phospholipase $A_1$ from ciliates. In particular, the phospholipase $A_1$ has the amino acid sequence SEQ ID No. 7.

10 Claims, 4 Drawing Sheets

Fig. 1

```
                                        aa  tat tta tca atg cta ctt ata att ctt tta gta -241
tga gat atg ata tgc tct ttc tct gct aga ctt aac tta tga cat ttg aac ttt taa taa -181
aag aat ttt ttt tat taa aaa gca gag att ttt aat aga aga atc aat gac tca tga att -121
taa taa aga ttt tca agt gtt ttc taa tac cga cta gct tta taa att cac tta tta atc -61
aac gat ata aaa att ata tta aca aat caa taa ata aaa aaa taa ata aaa aca aaa caa -1
ATG AAC AAG ACT CTC ATC TTA GCT TTA GTT GTT GTT TTG GCT TTA ACT GCC ACC ACC TTG 60
GTT GCT TTC CAC AAC CAC TCT CAC AAC ATC AGA GTT GAC TAA GAC CCC GCC ACT CTC TTC 120
AAG CAA TTC AAG CAA ACT TAC AAT AAG AAG TAT GCT GAT GCT ACT TTC GAA ACC TAC AGA 180
TTC GGT GTC TTC ACC CAA AAC TTA GAA ATC GTC AAG ACT GAC TCT ACT TTG GGT GTC ACC 240
TAA TTC ATG GAC TTA ACT CCT GCT GAA TTC GCT CAA CAA TTC CTC ACT TTA CAC GAA AAG 300
GTT AAC AGC ACC GAA GTT TAC AGA GCT TAA GGT GAA GCT ACC GAA GTT GAC TGG ACT GCC 360
AAG GGT AAG GTC ACC CCT GTT AAG AAC TAA GGT TCT TGT GGT TCC TGC TGG GCT TTC TCC 420
ACC ATT GGT GCC GTT GAA TCT GCT CTT TGG ATT GCT GGT CAA GGT GAA TAA AAC ACT CTT 480
AAC CTT GCT GAA TAA GAA TAA GTT GAC TGT GCT AAG TCC CCC AAG TAC GAC TCT GAA GGT 540
TGC AAC GGT GGT TGG ATG GTT GAA GGT TTC AAG TAC ATC ATC GAC AAC AAG ATC TCC TAA 600
ACT GCT AAC TAT CCC TAC ACT GCT AAG GAT GGT AAG TGC AAG GAC ACC TCT CCT TCA AAG 660
AAG TTC TCT ATT TCT AAG TAC GCT GAA ATC CCC TAA GGT GAC TGC AAC TCC CTC AAC TCT 720
GCC TTA GAA CAA GGT CCT ATC TCC GTT GCT GTT GAT GCC ACC AAC TTC TAA TTC TAC ACT 780
TCT GGT GTC TTT AAA AAC TGC AAG GCC AAC CTC AAC CAC GGT GTC CTC TTA GTT GCC AAC 840
GTT GAC TCT TCT CTC AAG ATC AAG AAC TCC TGG GGT CCT TCT TGG GGT GAA AAG GGT TTC 900
ATC AGA TTA GCT GCC GGT AAC ACT TGC GGT GTC TGC AAT GCT GCC TCT TAC CCT ATT GTT 960
TGA aaa aac ata atc caa att aaa aaa aat tac tca aaa ctg ata ata taa aaa att aat 1020
ttt cat aat ttt aat gta aat aaa tac ctt tat att tga cgt ttt gta ctc aaa ata aat 1080
taa agt taa caa acc ata ttt att taa ttc tac ttt tca att ttt aaa aat ata         1140
```

Fig. 2:

Die Aminosäure-Sequenz der Phospholipase A₁ aus *Tetrahymena*:Prä/Propeptid (Aminsäure 1 bis 110):

| M | N | K | T | L | I | L | A | L | V | G | V | L | A | L | 15 |
| T | A | T | T | L | V | A | F | H | N | H | S | H | N | I | 30 |
| R | V | D | Q | D | P | A | T | L | F | K | Q | F | K | Q | 45 |
| T | Y | N | K | K | Y | A | D | P | T | F | E | T | Y | R | 60 |
| F | G | V | F | T | Q | N | L | E | I | V | K | T | D | S | 75 |
| T | F | G | V | T | Q | F | M | D | L | T | P | A | E | F | 90 |
| A | Q | Q | F | L | T | L | H | E | K | V | N | S | T | E | 105 |
| V | Y | R | A | Q | | | | | | | | | | | 110 |

Reifes Protein (vom N-Terminus bis zum C-Terminus, Aminosäure 111 bis 342):

| G | E | A | T | E | V | D | W | T | A | K | G | K | V | T | 125 |
| P | V | K | N | Q | G | S | C | G | S | C | W | A | F | S | 140 |
| T | I | G | A | V | E | S | A | L | L | I | A | G | Q | G | 155 |
| E | Q | N | T | L | N | L | A | E | Q | E | L | V | D | C | 170 |
| A | K | S | P | K | Y | D | S | E | G | C | N | G | G | W | 185 |
| M | V | E | G | F | K | Y | I | I | D | N | K | I | S | Q | 200 |
| T | A | N | Y | P | Y | T | A | K | D | G | K | C | K | D | 215 |
| T | S | S | F | K | K | F | S | I | S | K | Y | A | E | I | 230 |
| P | Q | G | D | C | N | S | L | N | S | A | L | E | Q | G | 245 |
| P | I | S | V | A | V | D | A | T | N | F | Q | F | Y | T | 260 |
| S | G | V | F | K | N | C | K | A | N | L | N | H | G | V | 275 |
| L | L | V | A | N | V | D | S | S | L | K | I | K | N | S | 290 |
| W | G | P | S | W | G | E | K | G | F | I | R | L | A | A | 305 |
| G | N | T | C | G | V | C | N | A | A | S | Y | P | I | V | 320 |

Stop                                                                 335

Figur 3: HIC I, Elutionsprofil, Natriumacetat-Gradient und Enzymaktivität der eluierten PLA₁
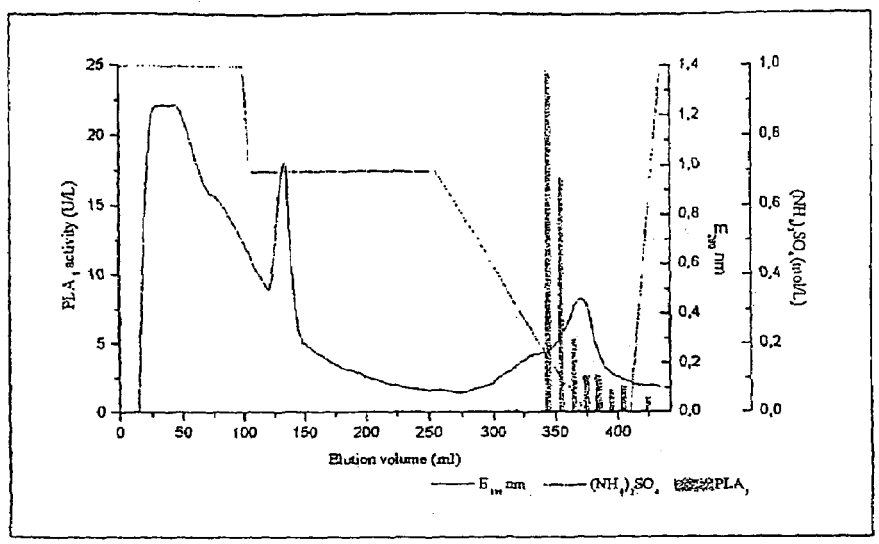
Figur 4: AEC, Ellutionsprofil, NaCl-Gradient und Enzymaktivität der eluierten PLA₁
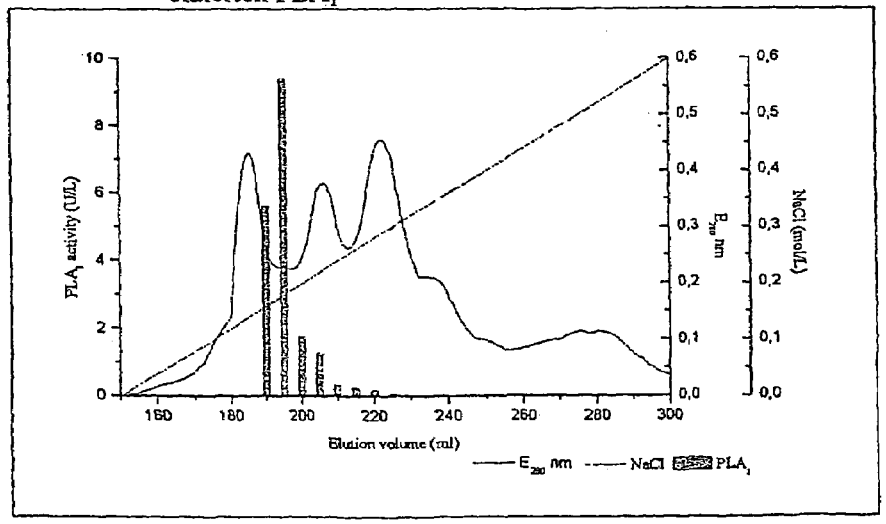

Figur 5: SEC, Elutionsprofil und Enzymaktivitäten der PLA₁
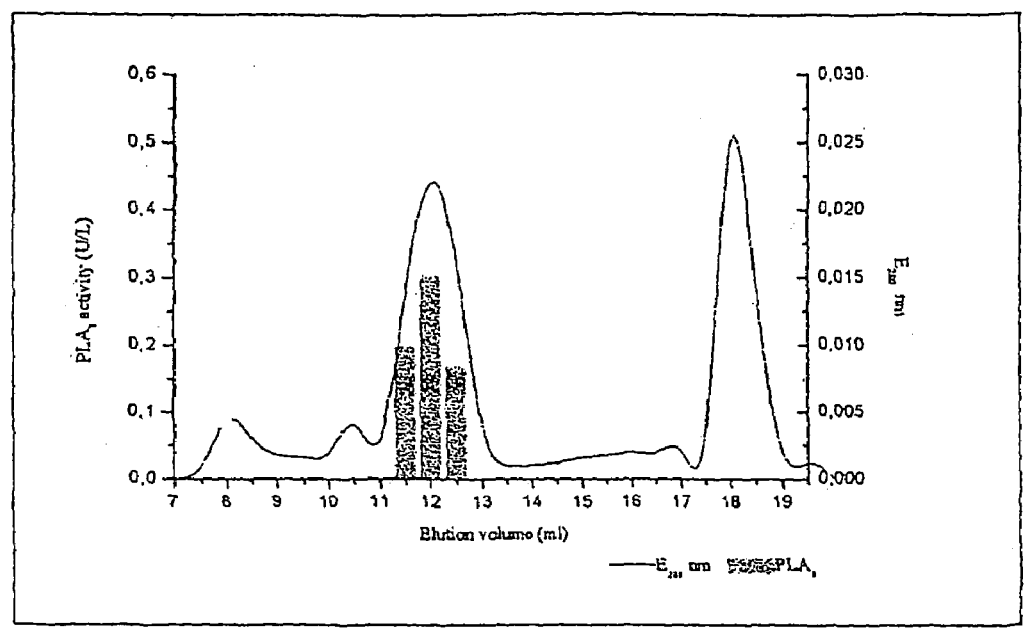

DNA SEQUENCE OF THE ENZYME PHOSPHOLIPASE A1 OF CILIATE TETRAHYMENA, AND THE USE OF THE SAME

The invention relates to a nucleic acid coding for the phospholipase A1 and the use thereof according to the preamble of claims 1 to 5.

Yeasts, bacteria and mammal cells are of great importance to the biotechnological preparation and production of recombinant active substances by the heterologous expression of foreign proteins. Bacterial expression systems based on *E. coli* or *B. subtilis* are used for the production of recombinant peptides or proteins, such as insulin, interleukin-2, tissue plasminogen activator, proteases and lipases. In Gram-negative bacteria, the expression systems are mostly based on the use of genetic elements, such as the lac operon or the tryptophan operon. The proteins foreign to the host are produced either into "inclusion bodies" within the cell, or when expression systems based on β-lactamase genes are used, into the periplasmic space. The production of recombinant proteins into the surrounding fermentation medium has not been established. In Gram-Positive bacteria, to date, almost exclusively cell-inherent proteins are introduced in expression systems and expressed.

Yeasts, such as *S. cerevisiae, Hansenula polymorpha, Kluyveromyces lactis* or *Pichia pastoris*, are also employed for the heterologous expression of recombinant proteins, such as human factor XIIIa, bovine pro-chymosin, phytase or surface antigens. Here, the expression systems are based on shuttle vectors (vectors having both yeast and bacterial portions) which are based (depending on the yeast species) on the genetic elements of galacto-kinase-epimerase, methanol oxidase, acid phosphatase or alcohol-dehydrogenase. As a rule, the recombinant protein is produced into the cytoplasm of the cell. When yeast-inherent signal sequences, such as the alpha factor, are used, the expressed proteins may also be secreted into the fermentation medium. The glycosylation of secreted proteins is effected according to the "high mannose" type, and frequently there are hyperglycosylations on the protein which may result in the formation of antibodies in the patient.

Mammal cells, such as various cell types from rodents (CHO cells, C127 cells) or simians (vero, CV-1 or COS cells) are also employed for the heterologous expression of recombinant proteins. Here, the expression systems are based on recombinant viruses (BPV vector) or on shuttle vectors. To regulate the expression, viral SV40 enhancer/promoter systems or cellular enhancer elements are employed. The recombinant proteins, such as erythropoietin, are secreted into the fermentation medium because the foreign genes usually bring their own signal sequences, which are understood by the expression system and used for targeting.

Further, for the biotechnological production of glycosylated extracellular enzymes, protozoans of the genus *Tetrahymena* are employed. *Tetrahymena* will grow on inexpensive fermentation media using standard fermentation methods. For the transformation of such *Tetrahymena* cells, vectors are available which are based on the rDNA elements of *Tetrahymena*. For the heterologous expression of bacterial proteins in *Tetrahymena*, DNA constructs made from genes from *Tetrahymena* are employed. When suitable genetic elements for the regulation of the transcription, targeting and glycosylation of foreign proteins are available, *Tetrahymena* is an ideal expression system for the inexpensive production of therapeutic recombinant proteins.

The Gram-negative bacterial expression systems used to date usually lead to the formation of "inclusion bodies" in the cell, accompanied by a denaturing of the proteins. To recover the recombinant protein, the cells must be lysed, and the denatured inactive protein must be folded back to function. This causes additional cost-intensive process steps and reduces the yield of the desired protein. Glycosylation, which is important to eukaryotic proteins, is completely omitted. When Gram-positive bacterial expression systems are used, degradation of the target protein due to high proteolytic activities in the fermentation broth is an additional problem.

When yeasts are used for heterologous expression, the desired target protein is also produced only into the cell, from where it must be removed by cell lysis. As in bacterial expression systems, this causes additional time- and cost-intensive process steps. When yeast-inherent signal peptides are used, the foreign proteins are not correctly spliced and glycosylated for secretion.

In contrast, when mammal cell systems are employed for the production of recombinant proteins, the desired proteins are found in the fermentation medium in an extracellular state, correctly spliced and glycosylated. However, what is disadvantageous here is, on the one hand, the low expression rate due to the defective processing and inefficient translation of genes which have been introduced into the genome of the production cell line via viral vectors. On the other hand, the serum-containing fermentation media for mammal cells are extremely cost-intensive. In addition, the fermentation technology for the shear-sensitive cell lines is complicated and similarly expensive due to constructions for bubble-free aeration. Further problems arise from the high infection risk for the cell lines from mycoplasmas and viruses. All in all, the use of mammal cells for the biotechnological preparation of recombinant proteins results in very high costs, safety demands and low yields.

To the use of ciliates, such as *Tetrahymena*, the above mentioned drawbacks in the production of recombinant proteins do not apply. Thus, for example, some acid hydrolases which are involved in the digestion of food particles are exported from the cell in high quantities and with complex glycosylation.

In J. Euk. Microbiol. 43 (4), 1996, pages 295 to 303, Alam et al. describe the cloning of a gene which codes for the acid α-glucosidase of *Tetrahymena pyriformis*. However, only a small portion of the protein is exported from the cell. Further, the International Patent Application PCT/EP 00/01853 describes the gene of a β-hexosaminidase from *Tetrahymena thermophila* which is known, however, to be exported from the cell to only about 80%.

However, to date, it has not been possible to cause glycosylated eukaryotic proteins to be expressed in *Tetrahymena* and also be exclusively secreted into the fermentation medium. This is because the DNA sequences of extracellular proteins inherent to *Tetrahymena* which are necessary for the construction of expression vectors and which exclusively export the foreign protein into the surrounding fermentation medium have as yet been unknown. The DNA sequences of a protein which codes for the β-hexosaminidase of *Tetrahymena thermophila* are known. Such a sequence has been filed for a patent application under the official file numbers DE 199 58 979.8, DE 199 09 189.7 and under PCT/EP 00/01853. However, there is a disadvantage of these sequences in that the pre/pro-peptides containing them will target a protein foreign to the host into the surrounding fermentation medium to only about 80%. This is due to the fact that the enzyme β-hexosaminidase is present to about 20% within the membrane under natural conditions, and only about 80% of the naturally produced enzyme is exported from the cell. For this reason, pre/pro peptides of β-hexosaminidase, when positioned in front of a protein foreign to the host by genetic engineering methods, will target, only about 20% of this protein foreign to the host into the cytoplasma membrane on the surface of *Tetrahymena thermophila*. This is associated with a considerable process-technological disadvantage for the production of recombinant active substances. On the one hand, the yield is decreased because part of the expressed protein remains in the cells bound to the membrane, and thus it is not possible to purify the entire expressed protein from the fermenter broth. On the other hand, the protein foreign to the host in the cell membrane can exert toxic effects on the host cells and thus slow down the cell growth.

Further, no constitutive promoters of *Tetrahymena* which cause a consistent or continuous transcription of heterologous proteins have been known to date. To date, only promoters of histone and tubulin genes have been known (Bannon et al., 1984, Gaertig et al., 1993). However, a critical disadvantage of these promoters is that their activation is dependent on the cell cycle. Genes of heterologous proteins which are linked to such cell-cycle-dependent promoters are caused to be expressed only in growing or dividing cells. This has considerable process-technological disadvantages since the desired protein is thus produced only in the logarithmic growth phase. In the stationary growth phase in which the highest cell density and thus the highest performance of the expression organism (*Tetrahymena*) is reached in the production process, there is hardly any cell growth left and thus only a low expression of the heterologous protein takes place.

It is an object of the invention to provide a system which enables the production of heterologous proteins in an expression system, after transformation into *Tetrahymena*, from the cells into the fermentation medium.

This object is achieved by a system in which a nucleic acid having the sequence SEQ ID No. 1 coding for a phospholipase A1 (SEQ ID No. 7) is employed. Advantageously, the expression product of this DNA is exported from the cell in large amounts under culturing conditions. The expressed protein is exported into the surrounding culture medium to a high extent and is not contained in the membrane. The nucleic acid sequence according to the invention contains a promoter which causes a constitutive, i.e., cell-cycle-independent, transcription of the downstream genes of heterologous proteins. Such constitutive transcription has the advantage that the proteins are continuously expressed by heterologous expression in the host organism without being affected by the cell cycle. Thus, the transcription of the foreign gene can be effected and the heterologous protein expressed also during the stationary growth phase with a low cell growth.

BRIEF DESCRIPTION OF THE DRAWINGS

FIG. 1 sequentially depicts a nucleic acid and its components.
FIG. 2 sequentially depicts polypeptide sequences.
FIG. 3 graphically illustrates an elution profile.
FIG. 4 graphically illustrates an elution profile.
FIG. 5 graphically illustrates an elution profile.

The DNA sequence of phospholipase $A_1$ according to the invention preferably includes an upstream region of $PLA_1$ (SEQ ID No. 2) which bears the promoter elements for the initiation of transcription, a signal peptide and a pro-peptide, further genetic elements for the targeting of proteins and, in particular, a down-stream region of $PLA_1$ (SEQ ID No. 3) which contains genetic elements for the termination of transcription. The use of these nucleic acids in a vector enables the expression of heterologously expressed proteins independently of the cell cycle and to transport them selectively out of the cell and into the surrounding culture medium without expressed proteins becoming incorporated in the cytoplasma membrane, whereby such proteins can be isolated from the fermentation broth without cell lysis.

FIG. 1 shows a nucleic acid coding for the upstream region (SEQ ID No. 2), the coding region (SEQ ID No. 1) and the downstream region (SEQ ID No. 3) of phospholipase $A_1$ from ciliates.

FIG. 2 shows a corresponding expression product of the nucleic acid according to SEQ ID No. 1. The invention also relates to the protein according to SEQ ID. No. 7.

In particular, the invention also relates to the signal sequence (SEQ ID No. 6) of the protein according to the invention. Preferably, these are the amino acids 1 to 110 of the protein according to the invention (SEQ ID No. 5). The invention also relates to a nucleic acid coding for the N-terminal fragment (SEQ ID No. 3). This is preferably a fragment of the nucleic acids according to the invention (SEQ ID No. 4), especially having the nucleic acid sequence 1 to 155 according to FIG. 1.

The nucleic acid sequence of the non-translated region (upstream region) (SEQ ID No. 2) upstream from the coding sequence region of the $PLA_1$ from *Tetrahymena* is positioned between position −275 and position −1 (represented in lowercase letters). The established non-translated region comprises 275 bases. As elements of a promoter, a TATA box is found on positions −49 to −55 (printed in boldface), and a putative CAAT box is found between base −133 and base −136 (printed in boldface). The coding sequence range of the cDNA is represented in capital letters. The numbering of the sequence begins with the start codon ATG. Regions known from protein sequencing are boxed, and the stop codon is underlined. The mature protein is coded from base 331. The sequence listing from base 1 to base 330 represents the pre/pro sequence (SEQ ID No. 8) of $PLA_1$. The sequence listing from base 331 to base 963 is the sequence of the mature $PLA_1$ (SEQ ID No. 9). In position 961, there is the translation stop TGA, and in position 1039, there is the polyadenylation signal AAT AAA. The nucleic acid sequence from position 964 to position 1134, which is below the coding sequence of the $PLA_1$ of *Tetrahymena*, represents the downstream region of $PLA_1$ (SEQ ID No. 3) which is not translated (also represented in lowercase letters). In position 964 to position 1101, there is the region known from the sequencing of the cDNA, which was also confirmed by inverse PCR. After transcription, the poly-A tail is attached to the last codon of the mRNA (ttt, positions 1098–1101).

A further aspect of the invention is the use of a nucleic acid sequence of acid hydrolases according to the invention or parts thereof for the homologous or heterologous expression of recombinant proteins and peptides, and for homologous or heterologous recombination ("knock-out, "gene replacement").

The invention also relates to a method for the homologous or heterologous expression of proteins and peptides and for the homologous or heterologous recombination ("knock-out, "gene replacement") in which ciliates are transfected with a nucleic acid according to the invention.

The nucleic acids or parts thereof may be combined, in particular, with the enhancers, promoters, operators, origins, terminators, antibiotic resistances usual for the homologous or heterologous expression of proteins, or with other nucleic acids or DNA fragments or all kinds of sequences from viroids, viruses, bacteria, archezoans, protozoans, fungi, plants, animals or humans.

In particular, the nucleic acid according to the invention is contained in a vector, a plasmid, a cosmid, a chromosome or minichromosome, a transposon, an IS element, an rDNA, or all kinds of circular or linear DNA or RNA.

The invention also relates to a method in which the nucleic acid or parts thereof according to the invention which code for phospholipase $A_1$ are combined with the usual, in homologous or heterologous expression, enhancers, such as the NF-1 region (a cytomegalovirus enhancer), promoters, such as the lac, trc, tic or tac promoters, the promoters of classes II and III of the T7 RNAP system, bacteriophage T7 and SP6 promoters, aprE, amylase or spac promoters for *Bacillus* expression systems, AOX1, AUG1 and 2 or GAPp promoters (*Pichia*) for yeast expression systems, RSV promoter (SV40 virus), CMV promoter (Cytomegalovirus), AFP promoter (adenoviruses) or metallothionine promoters for mammal expression systems, Sindbis virus promoters or Semlike forest virus promoters for insect cells, promoters for insect cell expression systems, such as hsp70, DS47, actin 5C or copia, plant-specific promoters, such as 35S promoter (cauliflower mosaic virus), amylase promoter or class I patatin promoter, operators, such as the tet operator, signal peptides, such as a-MF prepro signal sequences (*Saccharomyces*), origins, terminators, antibiotic and drug resistances, such as ampicillin, kanamycin, streptomycin, chloramphenicol, penicillin, amphotericin, cycloheximide, 6-methylpurine, paromomycin, hygromycin, α-amanatin, auxotrophy markers, such as the gene of dihydrofolate reductase, or other nucleic acids or DNA fragments, or all kinds of sequences from viroids, viruses, bacteria, archezoans, protozoans, fungi, plants, animals or humans.

In particular, the nucleic acid or parts thereof according to the invention are inserted into a vector, a plasmid, a cosmid, a chromosome or minichromosome, a transposon, an IS element, an rDNA, or all kinds of circular or linear DNA or RNA.

The skilled person will understand that nucleic acids having at least 40% homology with the nucleic acid according to SEQ ID No. 1 can also be employed according to the invention. The protein according to SEQ ID No. 2 can also be modified without losing its function. Thus, for example, so-called conservative exchanges of amino acids may be performed. Thus, for example, hydrophobic amino acids can be interchanged.

For the purification and isolation of phospholipase $A_1$ from *Tetrahymena* and for determining its sequence, the following methods can be used.

Recovery of $PLA_1$

PLA1 was obtained from cell-free culture supernatants of *Tetrahymena thermophila*. Thus, the cells were fermented in a 2 I fermenter (Biostat MD, Braun Diessel Biotech, Melsungen, Germany) which was controlled over a digital controlling unit (DCU). The fermenter was first operated for 24 hours in a batch operation and then continuously. Harvesting of the cell-free culture supernatant was ensured through a perfusion module having a pore size of about 0.3 µm (S6/2, Enka, Wuppertal).

The fermentation was performed under the following parameters:
 the working volume was 2 liters;
 the perfusion rate was 2 liters/day;
 the revolutions per minute of the stirrer was limited to 800 rpm;
 the temperature was constantly at 30° C.;
 the pH value was kept constant at pH 7;
 the inoculation titer was at 50,000 cells/ml.

For the fermentation, the strain SB 1868 VII was used. This is a wild type strain of *Tetrahymena thermophila*.

The fermentation was performed over a period of 264 hours, and the harvests were tested for $PLA_1$ activity.

Purification of $PLA_1$

For the purification of $PLA_1$, 1 liter of cell-free culture supernatant from the fermentation was used. It was admixed with 140 g of ammonium sulfate and concentrated through an ultrafiltration unit (Pellikon XL, exclusion size 3 kDa, Millipore) to a volume of 50 ml. Subsequently, the sample was purified by hydrophobic interaction chromatography (20×1.6 Fractogel EMD Phenyl I 650, Merck, Darmstadt). The flow rate was 5 ml/min, and the eluate was collected in 5 ml fractions. The enzyme activity was measured by the deacylation of a radioactively labeled phospholipid (L-3-phosphatidylcholine, 1-palmitoyl-2-[1-$^{14}$C]linoleoyl). FIG. 3 shows the elution profile obtained, the sodium acetate gradient and the enzyme activities in the individual fractions.

The three fractions having the highest enzyme activities were combined and rebuffered into the starting buffer (Bis-Tris 20 mM, pH 6.5) for anion-exchange chromatography (AEC) by means of an ultrafiltration unit. Subsequently, the sample was charged onto the column (Q-Sepharose-Hiload-16/10, Pharmacia, Sweden), and the $PLA_1$ was eluted with a linear NaCl gradient (flow rate=3 ml/min) from the column and collected in 5 ml fractions. FIG. 4 shows the elution profile obtained, the NaCl gradient and the enzyme activities of the individual fractions.

From the fraction having the highest $PLA_1$ activity, 200 µl was removed and separated by size exclusion chromatography (SEC). For this purpose, a Superdex HR 75 30/10 column (Pharmacia, Sweden) was used. The flow rate in this chromatography was 0.6 ml/min, the eluate was collected in 200 µl fractions. FIG. 5 shows the elution profile obtained and the enzyme activities of the individual fractions.

The fractions obtained were examined for their purity using one-dimensional gel electrophoresis. Thus, two distinct bands were established at ~26 and ~28 kDa. Separation of these two bands by a two-dimensional gel electrophoresis resulted in a separation of the two bands into 2 and 3 spots, respectively, having different isoelectric points.

For the 26 kDa proteins, these were at pH 6.3 and 5.7, and for the 28 kDa proteins, they were at pH 6.3, 5.7 and 5.3. A final examination of these spots by mass fingerprint analysis showed, that these spots were isoforms of the same protein.

Molecular-Biological Examination of $PLA_1$

After the purity of the protein had been demonstrated, samples of the protein were blotted onto a PVDF membrane and subjected to initial sequencing from the N terminus. In addition, a further sample was tryptically digested and also subjected to initial sequencing. Using the protein sequences obtained thereby, oligonucleotide primers were prepared, which were then employed in reverse transcriptase PCR (3' RACE, rapid amplification of cDNA ends). Using this PCR technique, cDNA of phospholipase $A_1$ was successfully amplified and subsequently sequenced. The sequence obtained had a length of 633 bases and 729 bases, respectively, and the molecular weight of the mature protein derived therefrom is about 22.4 kDa. In the sequence derived, the oligopeptides of 22 amino acids (N-terminal)

and 18 amino acids (within the protein) established from protein sequencing were found again to 100%. In addition to the sequence of the mature protein, the sequence of the pre/pro peptide could also be established by means of 5' RACE (rapid amplification of cDNA ends) (FIG. 2). This is a peptide having a length of 110 amino acids which bears both the signal sequence and the pro peptide which inactivates the enzyme and is cleaved off only at the final place of activity of the enzyme.

Sequence comparisons yielded no homologies with previously known phospholipases $A_1$, except for a consensus sequence of 5 amino acids (G×S×G), which is found in all lipases and phospholipases and is discussed as a binding site for lipids or phospholipids. Further, the upstream and downstream sequences of $PLA_1$ were established by inverse PCR (FIG. 1). Thus, genomic DNA was cut with restriction endonucleases, ligated with T4 ligase and finally amplified with inverse primers. For the amplification of the upstream region of $PLA_1$ by inverse PCR, genomic DNA cut with the restriction endonuclease SspI was used. Thus, an upstream region of 275 bases could be established, and promoter elements identified. In position −136, there is a CAAT box which has a similar distance from the translation start as the CCAAT boxes of the histone genes (−141 and −151) of *Tetrahymena* as found by Brunk and Sadler (1990). A TATA box, which fixes the exact starting point of transcription in eukaryotic genes, was identified on position −55. Its sequence corresponds to the consensus sequences found in eukaryotes. For the amplification of the downstream region, which contains the terminator for the transcription of the $PLA_1$ from *Tetrahymena*, by inverse PCR, genomic DNA cut with BamHI was used. Thus, in addition to the downstream region known from 3'-RACE, another 222 bases could be established (FIG. 3).

The invention claimed is:

1. An isolated nucleic acid sequence of SEQ ID NO: 4, consisting of coding and non-coding regions, wherein the coding region codes for phospholipase A1 (PLA$_1$) from *Tetrahymena thermophila* (SEQ ID NO: 5), and non-coding regions represent the upstream and downstream regions of the phospholipase A$_1$ gene.

2. An isolated nucleic acid sequence of SEQ ID NO: 2 or SEQ ID NO: 3.

3. An isolated nucleic acid sequence of SEQ ID NO: 1, SEQ ID NO: 8 or SEQ ID NO: 9.

4. An isolated signal sequence of the PLA$_1$ (SEQ ID NO: 5) having the sequence of SEQ ID NO: 6.

5. An isolated PLA$_1$ protein having the sequence of SEQ ID NO: 7.

6. A method for homologous or heterologous expression of a protein comprising transfecting a ciliate host cell with the nucleic acid of claim 1 and culturing the host cell under conditions allowing expression of phospholipase A$_1$.

7. The method according to claim 6, wherein the transfected nucleic acid is contained in a vector, plasmid or a cosmid.

8. A method for homologous or heterologous expression of a protein comprising transfecting a ciliate host cell with the nucleic acid of claim 3 and culturing the host cell under conditions allowing expression of phospholipase A$_1$.

9. A transformed vector, plasmid or cosmid, comprising the nucleic acid of claim 1.

10. A transformed vector, plasmid or cosmid, comprising the nucleic acid of claim 3.

* * * * *

UNITED STATES PATENT AND TRADEMARK OFFICE
CERTIFICATE OF CORRECTION

PATENT NO. : 7,045,330 B2
APPLICATION NO. : 10/466110
DATED : May 16, 2006
INVENTOR(S) : Hartmann et al.

It is certified that error appears in the above-identified patent and that said Letters Patent is hereby corrected as shown below:

In the drawing, Sheet 2, change "Die Aminosäure-Sequenz der Phospholipase $A_1$ aus *Tetrahymena*: Prä/Propeptid (Aminsäure 1 bis 110)" to --The amino acid sequence of the phospholipase $A_1$ from *Tetrahymena* pre/pro peptide (amino acid 1 to 110)--; change "Reifes Protein (vom N-Terminus bis zum C-Terminus, Aminosäure 111 bis 342)" to --Mature protein (from the N-terminus to the C-terminus, amino acids 111 to 342)--.

In the drawing, Sheet 3, change "Figur 3: HIC 1, Elutionsprofil, Natriumacetat-Gradient und Enzymaktivität der eluierten $PLA_1$" to --Figure 3: HIC I, elution profile, sodium acetate gradient and enzyme activity of eluted $PLA_1$--; change "Figur 4: AEC, Ellutionsprofil, NaCl-Gradient und Enzymaktivität der eluierten $PLA_1$" to --Figure 4: AEC, elution profile, NaCl gradient and enzyme activity of eluted $PLA_1$--.

In the drawing, Sheet 4, change "Figur 5: SEC, Elutionsprofil und Enzymakivitäten der $PLA_1$" to --Figure 5: SEC, elution profile and enzyme activities of $PLA_1$--.

Signed and Sealed this

Seventeenth Day of April, 2007

JON W. DUDAS
*Director of the United States Patent and Trademark Office*

SEQUENCE LISTING

<160> NUMBER OF SEQ ID NOS: 9

<210> SEQ ID NO 1
<211> LENGTH: 963
<212> TYPE: DNA
<213> ORGANISM: Tetrahymena thermophila

<400> SEQUENCE: 1

```
atgaacaaga ctctcatctt agctttagtt gttgttttgg ctttaactgc caccaccttg      60
gttgctttcc acaaccactc tcacaacatc agagttgact aagaccccgc cactctcttc     120
aagcaattca agcaaactta caataagaag tatgctgatg ctactttcga aacctacaga     180
ttcggtgtct tcacccaaaa cttagaaatc gtcaagactg actctacttt cggtgtcacc     240
taattcatgg acttaactcc tgctgaattc gctcaacaat tcctcacttt acacgaaaag     300
gttaacagca ccgaagttta cagagcttaa ggtgaagcta ccgaagttga ctggactgcc     360
aagggtaagg tcacccctgt taagaactaa ggttcttgtg gttcctgctg ggctttctcc     420
accattggtg ccgttgaatc tgctctttgg attgctggtc aaggtgaata aaacactctt     480
aaccttgctg aataagaata agttgactgt gctaagtccc ccaagtacga ctctgaaggt     540
tgcaacggtg gttggatggt tgaaggtttc aagtacatca tcgacaacaa gatctcctaa     600
actgctaact atccctacac tgctaaggat ggtaagtgca aggacacctc ttccttcaag     660
aagttctcta tttctaagta cgctgaaatc ccctaaggtg actgcaactc cctcaactct     720
gccttagaac aaggtcctat ctccgttgct gttgatgcca ccaacttcta attctacact     780
tctggtgtct ttaaaaactg caaggccaac ctcaaccacg gtgtcctctt agttgccaac     840
gttgactctt ctctcaagat caagaactcc tggggtcctt cttgggtgtga aaagggtttc     900 atcagattag ctgccggtaa cacttgcggt gtctgcaatg ctgcctctta ccctattgtt     960
tga                                                                 963
```

<210> SEQ ID NO 2
<211> LENGTH: 275
<212> TYPE: DNA
<213> ORGANISM: Tetrahymena thermophila

<400> SEQUENCE: 2

```
aatatttatc aatgctactt ataattcttt tagtatgaga tatgatatgc tctttctctg      60
ctagacttaa cttatgacat ttgaacttt aataaaagaa ttttttttat taaaaagcag     120
```

-continued

```
agatttttaa tagaagaatc aatgactcat gaatttaata aagattttca agtgttttct    180
aataccgact agctttataa attcacttat taatcaacga tataaaaatt atattaacaa    240
atcaataaat aaaaaaataa ataaaaacaa aacaa                               275

<210> SEQ ID NO 3
<211> LENGTH: 171
<212> TYPE: DNA
<213> ORGANISM: Tetrahymena thermophila

<400> SEQUENCE: 3
aaaaacataa tccaaattaa aaaaaattac tcaaaactga taatataaaa aattaatttt     60
cataatttta atgtaaataa ataccttat atttgacgtt ttgtactcaa aataaattaa    120
agttaacaaa ccatatttat ttaattctac ttttcaattt ttaaaaatat a             171

<210> SEQ ID NO 4
<211> LENGTH: 1408
<212> TYPE: DNA
<213> ORGANISM: Tetrahymena thermophila

<400> SEQUENCE: 4
aatatttatc aatgctactt ataattcttt tagtatgaga tatgatatgc tctttctctg     60
ctagacttaa cttatgacat tgaacttttt aataaaagaa ttttttttat taaaaagcag    120
agatttttaa tagaagaatc aatgactcat gaatttaata aagattttca agtgttttct    180
aataccgact agctttataa attcacttat taatcaacga tataaaaatt atattaacaa    240
atcaataaat aaaaaaataa ataaaaacaa aacaaatgaa caagactctc atcttagctt    300
tagttgttgt tttggcttta actgccacca ccttggttgc tttccacaac cactctcaca    360
acatcagagt tgactaagac cccgccactc tcttcaagca attcaagcaa acttacaata    420
agaagtatgc tgatgctact ttcgaaacct acagattcgg tgtcttcacc caaaacttag    480
aaatcgtcaa gactgactct actttcggtg tcacctaatt catggactta actcctgctg    540
aattcgctca acaattcctc actttcacga aaggttaac agcaccgaag tttacagagc    600
ttaaggtgaa gctaccgaag ttgactggac tgccaagggt aaggtcaccc ctgttaagaa    660
ctaaggttct tgtggttcct gctgggcttt ctccaccatt ggtgccgttg aatctgctct    720
ttggattgct ggtcaaggtg aataaaacac tcttaacctt gctgaataag aataagttga    780
ctgtgctaag tcccccaagt acgactctga aggttcaac ggtggttgga tggttgaagg    840
tttcaagtac atcatcgaca acaagatctc ctaaaactgct aactatccct acactgctaa    900
ggatggtaag tgcaaggaca cctcttcctt caagaagttc tctatttcta agtacgctga    960
aatcccctaa ggtgactgca actccctcaa ctctgcctta gaacaaggtc ctatctccgt   1020
tgctgttgat gccaccaact tctaattcta cacttctggt gtctttaaaa actgcaaggc   1080
caacctcaac cacggtgtcc tcttagttgc aacgttgac tcttctctca agatcaagaa   1140 ctcctgggt ccttcttggg gtgaaaaggg tttcatcaga ttagctgccg gtaacacttg   1200
cggtgtctgc aatgctgcct cttaccctat tgtttgaaaa acataatcc aaattaaaaa   1260 aaattactca aaactgataa tataaaaaat taattttcat aattttaatg taaataaata   1320
cctttatatt tgacgttttg tactcaaaat aaattaaagt taacaaacca tatttattta   1380
attctacttt tcaattttta aaatata                                       1408

<210> SEQ ID NO 5
```

```
<211> LENGTH: 80
<212> TYPE: PRT
<213> ORGANISM: Tetrahymena thermophila

<400> SEQUENCE: 5

Ala Leu Glu Gln Gly Pro Ile Ser Val Ala Val Asp Ala Thr Asn Phe
1               5                   10                  15

Gln Phe Tyr Thr Ser Gly Val Phe Lys Asn Cys Lys Ala Asn Leu Asn
            20                  25                  30

His Gly Val Leu Leu Val Ala Asn Val Asp Ser Ser Leu Lys Ile Lys
        35                  40                  45

Asn Ser Trp Gly Pro Ser Trp Gly Glu Lys Gly Phe Ile Arg Leu Ala
    50                  55                  60

Ala Gly Asn Thr Cys Gly Val Cys Asn Ala Ala Ser Tyr Pro Ile Val
65                  70                  75                  80

<210> SEQ ID NO 6
<211> LENGTH: 110
<212> TYPE: PRT
<213> ORGANISM: Tetrahymena thermophila

<400> SEQUENCE: 6

Met Asn Lys Thr Leu Ile Leu Ala Leu Val Gly Val Leu Ala Leu Thr
1               5                   10                  15

Ala Thr Thr Leu Val Ala Phe His Asn His Ser His Asn Ile Arg Val
            20                  25                  30

Asp Gln Asp Pro Ala Thr Leu Phe Lys Gln Phe Lys Gln Thr Tyr Asn
        35                  40                  45

Lys Lys Tyr Ala Asp Pro Thr Phe Glu Thr Tyr Arg Phe Gly Val Phe
    50                  55                  60

Thr Gln Asn Leu Glu Ile Val Lys Thr Asp Ser Thr Phe Gly Val Thr
65                  70                  75                  80

Gln Phe Met Asp Leu Thr Pro Ala Glu Phe Ala Gln Gln Phe Leu Thr
                85                  90                  95

Leu His Glu Lys Val Asn Ser Thr Glu Val Tyr Arg Ala Gln
                100                 105                 110

<210> SEQ ID NO 7
<211> LENGTH: 210
<212> TYPE: PRT
<213> ORGANISM: Tetrahymena thermophila

<400> SEQUENCE: 7

Gly Glu Ala Thr Glu Val Asp Trp Thr Ala Lys Gly Lys Val Thr Pro
1               5                   10                  15

Val Lys Asn Gln Gly Ser Cys Gly Ser Cys Trp Ala Phe Ser Thr Ile
            20                  25                  30

Gly Ala Val Glu Ser Ala Leu Leu Ile Ala Gly Gln Gly Glu Gln Asn
        35                  40                  45

Thr Leu Asn Leu Ala Glu Gln Glu Leu Val Asp Cys Ala Lys Ser Pro
    50                  55                  60

Lys Tyr Asp Ser Glu Gly Cys Asn Gly Gly Trp Met Val Glu Gly Phe
65                  70                  75                  80

Lys Tyr Ile Ile Asp Asn Lys Ile Ser Gln Thr Ala Asn Tyr Pro Tyr
                85                  90                  95

Thr Ala Lys Asp Gly Lys Cys Lys Asp Thr Ser Ser Phe Lys Lys Phe
                100                 105                 110
```

-continued

Ser Ile Ser Lys Tyr Ala Glu Ile Pro Gln Gly Asp Cys Asn Ser Leu
        115                 120                 125

Asn Ser Ala Leu Glu Gln Gly Pro Ile Ser Val Ala Val Asp Ala Thr
    130                 135                 140

Asn Phe Gln Phe Tyr Thr Ser Gly Val Phe Lys Asn Cys Lys Ala Asn
145                 150                 155                 160

Leu Asn His Gly Val Leu Leu Val Ala Asn Val Asp Ser Ser Leu Lys
                165                 170                 175

Ile Lys Asn Ser Trp Gly Pro Ser Trp Gly Glu Lys Gly Phe Ile Arg
            180                 185                 190

Leu Ala Ala Gly Asn Thr Cys Gly Val Cys Asn Ala Ala Ser Tyr Pro
        195                 200                 205

Ile Val
    210

<210> SEQ ID NO 8
<211> LENGTH: 330
<212> TYPE: DNA
<213> ORGANISM: Tetrahymena thermophila

<400> SEQUENCE: 8

| | | | | | |
|---|---|---|---|---|---|
| atgaacaaga | ctctcatctt | agctttagtt | gttgttttgg | ctttaactgc | caccaccttg | 60 |
| gttgctttcc | acaaccactc | tcacaacatc | agagttgact | aagacccccgc | cactctcttc | 120 |
| aagcaattca | agcaaactta | caataagaag | tatgctgatg | ctactttcga | aacctacaga | 180 |
| ttcggtgtct | tcacccaaaa | cttagaaatc | gtcaagactg | actctacttt | cggtgtcacc | 240 |
| taattcatgg | acttaactcc | tgctgaattc | gctcaacaat | tcctcacttt | acacgaaaag | 300 |
| gttaacagca | ccgaagttta | cagagcttaa | | | | 330 |

<210> SEQ ID NO 9
<211> LENGTH: 633
<212> TYPE: DNA
<213> ORGANISM: Tetrahymena thermophila

<400> SEQUENCE: 9

| | | | | | |
|---|---|---|---|---|---|
| ggtgaagcta | ccgaagttga | ctggactgcc | aagggtaagg | tcacccctgt | taagaactaa | 60 |
| ggttcttgtg | gttcctgctg | ggcttctctcc | accattggtg | ccgttgaatc | tgctctttgg | 120 |
| attgctggtc | aaggtgaata | aaacactctt | aaccttgctg | aataagaata | agttgactgt | 180 |
| gctaagtccc | ccaagtacga | ctctgaaggt | tgcaacggtg | gttggatggt | tgaaggtttc | 240 |
| aagtacatca | tcgacaacaa | gatctcctaa | actgctaact | atccctacac | tgctaaggat | 300 |
| ggtaagtgca | aggacaccctc | ttccttcaag | aagttctcta | tttctaagta | cgctgaaatc | 360 |
| ccctaaggtg | actgcaactc | cctcaactct | gccttagaac | aaggtcctat | ctccgttgct | 420 |
| gttgatgcca | ccaacttcta | attctacact | tctggtgtct | ttaaaaactg | caaggccaac | 480 |
| ctcaaccacg | gtgtcctctt | agttgccaac | gttgactctt | ctctcaagat | caagaactcc | 540 |
| tggggtcctt | cttggggtga | aaagggtttc | atcagattag | ctgccggtaa | cacttgcggt | 600 |
| gtctgcaatg | ctgcctctta | ccctattgtt | tga | | | 633 |